(12) United States Patent
Shah et al.

(10) Patent No.: US 6,568,271 B2
(45) Date of Patent: May 27, 2003

(54) GUIDED ACOUSTIC WAVE SENSOR FOR PIPELINE BUILD-UP MONITORING AND CHARACTERIZATION

(75) Inventors: Vimal V. Shah, Houston, TX (US); James R. Birchak, Spring, TX (US); Wei Han, Missouri City, TX (US); Bruce H. Storm, Houston, TX (US); Rajnikant M. Amin, Houston, TX (US); Bayram Kalpakci, The Woodlands, TX (US); Fouad Fleyfel, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 68 days.

(21) Appl. No.: 09/850,962

(22) Filed: May 8, 2001

(65) Prior Publication Data

US 2003/0033870 A1 Feb. 20, 2003

(51) Int. Cl.$^7$ ............................................. G01N 29/20
(52) U.S. Cl. ........................................................ 73/599
(58) Field of Search .......................... 73/599, 597, 598, 73/600, 596, 622, 638

(56) References Cited

U.S. PATENT DOCUMENTS

| | | | |
|---|---|---|---|
| 4,490,679 A | | 12/1984 | Siller .......................... 324/446 |
| 4,805,156 A | | 2/1989 | Attali et al. .................... 367/35 |
| 4,843,247 A | | 6/1989 | Yamazoe et al. ............ 250/573 |
| 5,549,001 A | * | 8/1996 | Brokowski et al. ............ 73/598 |
| 5,629,485 A | * | 5/1997 | Rose et al. .................... 73/599 |
| 5,763,773 A | | 6/1998 | Birchak et al. ........... 73/152.58 |
| 5,892,162 A | | 4/1999 | Spinks et al. ............... 73/865.8 |
| 5,970,434 A | * | 10/1999 | Brophy et al. ................. 73/584 |
| 6,148,672 A | * | 11/2000 | Cawley et al. ................. 73/622 |

* cited by examiner

Primary Examiner—John E. Chapman
(74) Attorney, Agent, or Firm—Conley Rose, P.C.

(57) ABSTRACT

A system for monitoring the presence of deposits or buildup on the inside wall of a fluid-containing pipe comprises a pair of acoustic transmitters outside of the pipe and spaced apart along the length of the pipe and capable of transmitting an acoustic signal into the pipe wall, a pair of acoustic receivers outside of the pipe and spaced apart along the length of the pipe and capable of receiving an acoustic signal from the pipe wall, and a power source for causing the transmitters to transmit a signal. A method for monitoring the presence of deposits or buildup on the inside wall of a fluid-containing pipe, comprises (a) providing first and second acoustic transmitters outside of the pipe and spaced apart along the length of the pipe and capable of transmitting an acoustic signal into the pipe wall, (b) providing first and second acoustic receivers outside of the pipe and spaced apart along the length of the pipe and capable of receiving an acoustic signal from the pipe wall, (c) transmitting a first signal from the first transmitter, (d) measuring the amplitude of the first signal received at the first and second receivers as $A_{11}$ and $A_{12}$, respectively, (e) transmitting a second signal from the second transmitter, (f) measuring the amplitude of the second signal received at the first and second receivers as $A_{21}$ and $A_{22}$, respectively, and (g) calculating the attenuation of the signal over the length of pipe using the values of $A_{11}$, $A_{12}$, $A_{21}$ and $A_{22}$.

23 Claims, 2 Drawing Sheets

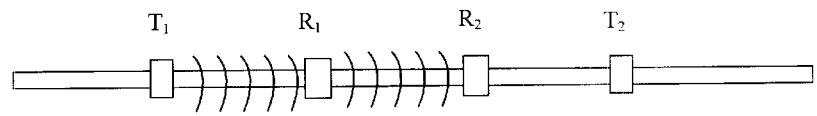
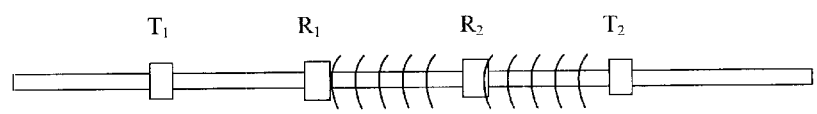
Fig.3
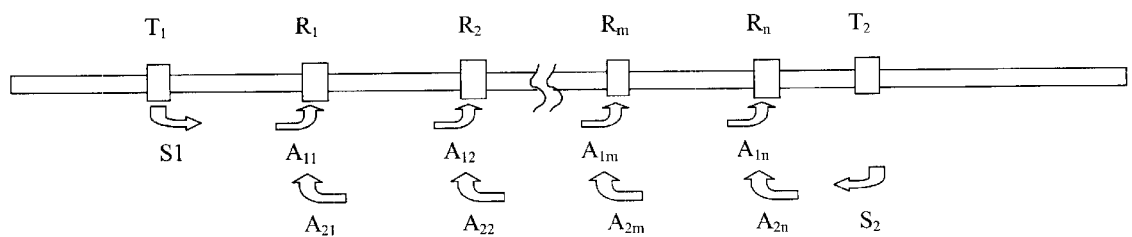
Fig.4
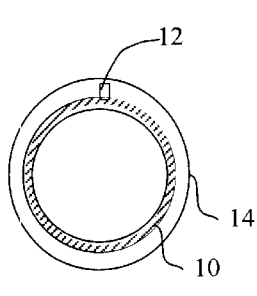 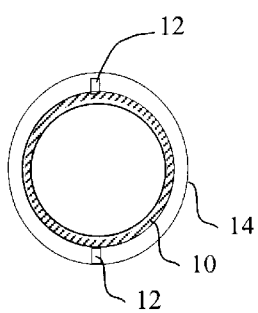 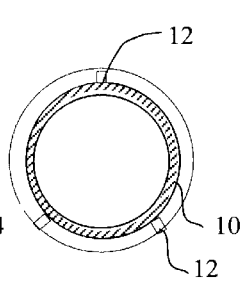 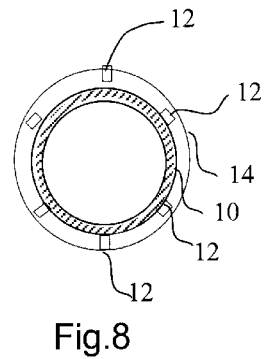
Fig.5　　　Fig.6　　　Fig.7　　　Fig.8

GUIDED ACOUSTIC WAVE SENSOR FOR PIPELINE BUILD-UP MONITORING AND CHARACTERIZATION

CROSS-REFERENCE TO RELATED APPLICATIONS

Not applicable.

STATEMENT REGARDING FEDERALLY SPONSORED RESEARCH OR DEVELOPMENT

Not Applicable.

BACKGROUND OF THE INVENTION

As the current trend in offshore oil and gas production advances into deeper waters, it is becoming increasingly necessary for the industry to develop cost effective solutions for developing fields in deep and/or remote waters.

A typical solution for such cases is to keep the production facilities on a "host platform" and connect the deep-water well(s) to the platform with pipelines and risers. The supporting equipment for the subsea tree control, such as hydraulic and electric power units, chemical injection pumps and tanks, and a control console, are also housed on the host platform. The subsea tree control is accomplished via long umbilical(s) consisting of electric conductors, hydraulic lines and chemical injection lines laid alongside the pipeline. In addition, two parallel pipelines are necessary to accomplish the roundtrip pigging operations. The distance between the well and the host platform is known as the tieback distance. The cost and technical challenges of this type of conventional tieback system increase as the tieback distance increases, and to a lesser extent as the water depth increases. In most cases, 20 miles represents the practical limit for the maximum tieback distance with the conventional tieback system.

One limit on the length of subsea tiebacks conveying crude petroleum arises from flow assurance problems. Solids such as asphaltene and paraffin deposit on the inner walls of the tiebacks and partially, and in some cases completely, block the flow. The longer the tieback is, the greater the length of pipe that must be inspected and kept free of deposits.

At present, non-intrusive sensors that can adequately detect and characterize such deposits are not available. The present solutions require use of very expensive alternative methods for flow assurance, including twin flowlines (for round-trip pigging), heat traced or insulated tiebacks. These alternative methods operate by attempting to prevent the deposition of solids on the flowline wall, and do not provide means for detecting the presence of solids in the event that deposits occur. The lack of continuous monitoring can result in undesirable shutdowns. For example, a flowline has been kept clear by pigging at a certain frequency, e.g. once per month, and the composition of the fluid in the flowline changes so that deposits begin to form at a greater rate, the line will become clogged and possible shut down because the previously established pigging frequency is now insufficient.

Guided acoustic waves similar those described in U.S. Pat. No. 5,892,162, have been used to detect corrosion in pipes based on reflections from corroded regions. Corrosion and scaling has also been detected in insulated pipelines on surface using guided waves and literature regarding this has been published from Imperial College, University of London.

Monitoring devices such as that described in U.S. Pat. No. 4,490,679 identify paraffin by monitoring change in the resistance of an electromagnetic coil. The monitoring device requires access to the fluid and is housed in a recess in the pipe. It is desired to provide monitoring without disrupting the flow of fluid through the line and without requiring direct contact with the fluid.

In U.S. Pat. No. 4,843,247, an optical asphaltene sensor is described. This sensor determines the content of asphaltene in heavy oils, based on the absorption spectra of asphaltene. The invention uses visible light in the region 500 nm to 1000 nm and thus requires at least optical access to the fluid. Furthermore, it does not distinguish between deposited and suspended asphaltene solids.

Hence, it is desired to provide a system that can operate over greater tieback distances without the cost and technical disadvantages that heretofore have prevented increasing the tieback distance. It is further desired to provide a method and apparatus for detecting deposits of asphaltene and paraffin on the inside wall of a pipeline that can be installed on a conventional pipeline and does not impede the flow of fluid through the pipeline. The desired system should be able to compensate for drift in the response of its components and should be capable of operating for a period of years without service or calibration.

SUMMARY OF THE INVENTION

The present invention provides a method and apparatus that allows longer tieback distances without the cost and technical disadvantages associated with previous methods. The present system detects deposits of asphaltene and paraffin on the inside wall of a pipeline without impeding the flow of fluid through the pipeline. Furthermore, the present system compensates for drift in the response of its components and is therefore capable of operating for a period of years without service or calibration.

In particular, the present system includes an acoustic sensor that is capable of detecting deposition and build-up of paraffin, asphaltene or hydrates on the inner walls of pipes, thus enabling timely intervention and flow assurance. In one embodiment, the sensor detects and monitors average deposition over a length of pipe. In another embodiment, multiple installations of the system allow the location of depositions to be determined with a desired degree of precision.

The present apparatus is capable of self-calibration and is not affected by drifts in equipment response that may be caused by variations in temperature or pressure or by the passage of time. The present sensors distinguish between types of deposition material based on the frequency and phase response.

In one embodiment, the present system is used to monitor and characterize the deposition and build-up of materials such as paraffin, asphaltene and hydrates in subsea tiebacks. Alternatively, the present system can be permanently installed in a borehole to monitor deposition. This sensor can also be used on surface pipelines to monitor deposition of solids in cases where solids deposition may occur, such as multiphase flow.

BRIEF DESCRIPTION OF THE DRAWINGS

In the detailed description of the present invention that follows, reference is made to the accompanying Figures, wherein:

FIG. 3 is a schematic illustration of a transmitter/receiver arrangement suitable for carrying out the present acoustic signaling;

FIG. 4 is a schematic illustration of opposed signals in the transmitter/receiver arrangement of FIG. 3; and FIGS. 5–8 are cross-sectional views of four exemplary arrangements of transducers on a pipe.

DETAILED DESCRIPTION OF THE PREFERRED EMBODIMENTS

The present invention comprises a non-invasive acoustic system for determining the presence of paraffinic or asphaltene deposits in a flowline. This approach uses a particular type of acoustic waves called guided acoustic waves or Lamb waves. Lamb waves describe acoustic waves travelling in a flat layer of finite thickness. Lamb predicted symmetric modes and anti-symmetric modes in what has become well-known in the art as Lamb wave dispersion curves. Lamb waves have been used in non-destructive testing to detect corrosion in pipes and to detect delaminations in aircraft panels.

Figure 1:
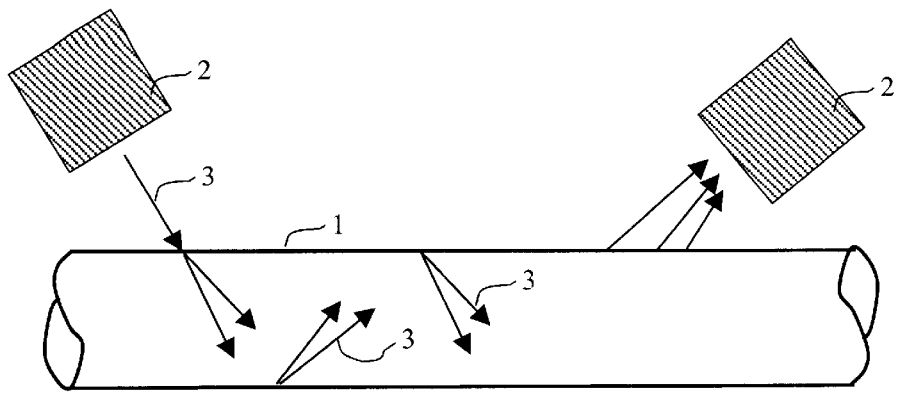
FIG. 1 is a schematic illustration of a tubular body receiving and transmitting acoustical waves.
Figure 2:
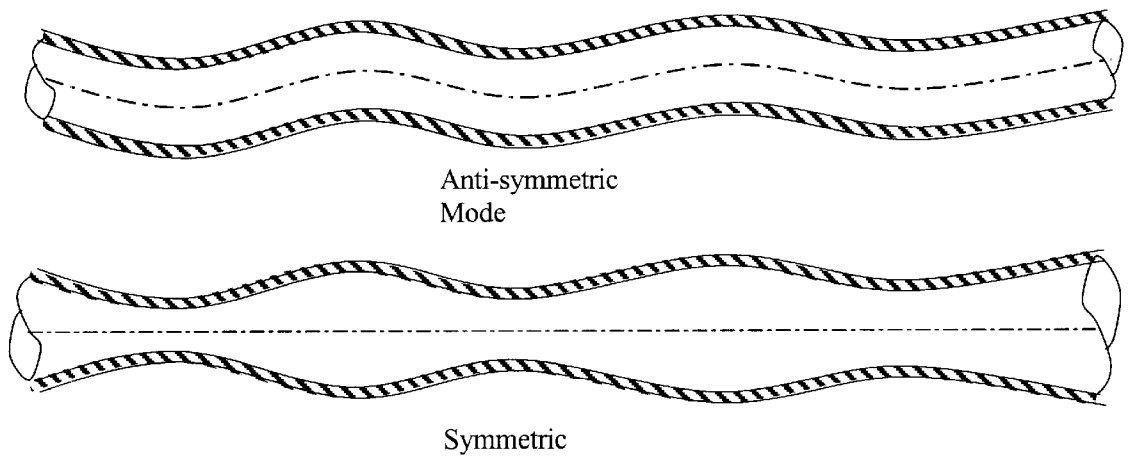
FIG. 2 is a schematic illustration of two transmission mechanisms for acoustical waves in a tubular body.

Guided acoustic waves (Lamb waves) develop when compression and transverse acoustic waves are trapped in thin members, also called wave-guides. The characteristics of guided waves are a function of the wave-guides themselves, as well as the boundary conditions of the wave-guides. As shown in FIG. 1, acoustic guided waves 3 can be generated when a transducer 2 sends compression acoustic signals into the wall of a tubular member 1, where they are converted to compression and transverse waves. After several reflections, guided waves are generated due to constructive and destructive interference. As shown schematically in FIG. 2, the resulting guided waves can be symmetric or anti-symmetric.

According to one embodiment and as shown in FIG. 3, the present system consists of two transmitters ($T_1$ and $T_2$) and at least two receivers ($R_1$ and $R_2$). Transmitters are placed at the beginning and end of the pipe section to be monitored. The section of pipe between the transmitters acts as a wave-guide and conveys the acoustic waves from the transmitters to the receivers. The length of the pipe section being monitored can vary from a few inches to several hundreds of feet, depending on the operating frequency of the acoustic waves and the resolution required from the sensor. Receivers $R_1$ and $R_2$ are placed between transmitters $T_1$ and $T_2$, and are preferably equidistantly spaced between transmitters $T_1$ and $T_2$. Receivers $R_1$ and $R_2$ detect solids deposited in the section of the pipe that lies between them. Thus, in the alternative embodiment shown in FIG. 4, n receivers $R_{1, 2 \ldots n}$ can be placed between two transmitters as shown, to detect and characterize finer variations in the deposition thickness and material properties. In each case, and regardless of how many receivers are used, the signal from each receiver that is associated with each transmitter provides an additional data point related to the extent of solid deposits in the length of pipe between the transmitters.

It should be noted that the duality of piezoelectric transducers is well known. Thus, a piezoelectric transmitter may be used as a receiver and vice versa, although this is not preferred in the present system.

Transmitter-receiver Arrangement

According to the preferred embodiments, the transmitters and receivers can be arranged in various configurations on the pipe section. FIGS. 5–8 illustrate a few of the several transmitter configurations that can be used to generate guided waves. In each of FIGS. 5–8, one or more transmitters 12 are positioned on the outside of a pipe 10. A casing or housing 14 is preferably, but not necessarily provided around the outside of transmitters 12. Each arrangement generates a preferential mode of guided waves at a particular frequency.

Alternative methods of generating guided waves using EMAT, piezoelectric and laser have been discussed in the prior art. While PZT ceramic is preferable in developing the transmitter, other piezoelectric or magnetostrictive materials can be used as well. Similarly, the receivers can be arranged to preferentially detect symmetric and anti-symmetric modes, based on the relative travel speeds of the different modes and the transverse displacement profile of the mode shapes.

According to a preferred embodiment, these configurations can be used, alone or in combination, to generate different modes of Lamb waves in pipes. Transmission of the Lamb waves is affected by the presence of deposits on the surface of the pipe, thereby making detection and characterization of the deposited layer(s) possible.

More specifically, guided waves generated at discrete frequencies interact uniquely with the deposition layer. Thus, in order to completely characterize the deposited layer, it is necessary to generate guided waves at various frequencies and ascertain the effect of the deposited layer on each of the generated modes at these frequencies. The present apparatus preferably operates at several different frequencies, and cycles through a preselected series of frequencies during operation.

The speeds, and correspondingly the arrival times, of various modes of guided wave propagation depend on the acoustic impedance of the pipe wall as well as on the acoustic impedance of the deposit layer. Acoustic impedance is a function of the layer density and speed of sound, which is an implicit function of the layer thickness. Attenuation is a function of surface traction (viscous drag) and radiation losses, which depend on the acoustic impedance of the deposit layer. Thus, by measuring the effect of the deposition layer on each mode or propagation, an inverse solution can be used to obtain the deposition layer thickness and properties.

Compensation Scheme

The present system is designed for prolonged use in a subsea environment. Over the life of the system, time and variations in temperature and pressure, as well as aging of transducer materials, will cause variations in the transmitters and receivers. Intervention in such environments for calibration or replacement of the sensor is uneconomical, if not impractical.

In order to compensate for variations in the transmitters and receivers, the present system provides a signal analysis technique that produces consistent results, regardless of drift in the transducers. A preferred embodiment of the present technique is as follows. For a particular mode, the received amplitude, frequency and arrival time observed at receiver $R_1$ for a wave travelling from transmitter $T_1$ are $A_{11}$, f, $\Delta t_{11}$ and $A_{12}$, f+$\Delta f_{12}$, $\Delta t_{12}$ at receiver $R_2$. Similarly for the same mode, the received amplitude, frequency and arrival time observed for a wave originating from transmitter $T_2$ are $A_{22}$, f, $\Delta t_{22}$ at receiver $R_2$ and $A_{21}$, f+$\Delta f_{21}$, $\Delta t_{21}$ at receiver $R_1$.

$A_{11}$ can be represented as $A_1 = A_0 e^{-\alpha x_{11}}$, where $x_{11}$ is the distance between transmitter $T_1$ and receiver $R_1$ and $\alpha$ is the attenuation coefficient. Similarly, $A_{12} = A_0 e^{-\alpha x_{12}}$, where $x_{12}$ is the distance between transmitter $T_1$ and receiver $R_2$. Rearranging these equations and eliminating $A_0$ gives $$\alpha = \frac{1}{(x_{12}-x_{11})} \ln\left(\frac{A_{11}}{A_{12}}\right).$$

For the acoustic wave originating from transmitter $T_2$, attenuation is obtained as $$\alpha = \frac{1}{(x_{22}-x_{21})} \ln\left(\frac{A_{22}}{A_{21}}\right),$$

where $x_{22}$ and $x_{21}$ are the distances of receivers $R_2$ and $R_1$ from transmitter $T_2$, respectively. Note that $x_{12}-x_{11}=x_{22}-x_{21}=X$, where X is the distance between receivers $R_1$ and $R_2$. Multiplying the two equations, the compensated attenuation is obtained as $$\alpha = \frac{1}{2X} \ln\left(\frac{A_{11}A_{22}}{A_{12}A_{21}}\right).$$

The attenuation coefficient calculated in this manner will remain accurate despite drift in the response of either transmitter or ether receiver. For example, if, over a period of time, the efficiency of receiver $R_1$ reduces to 90% and the efficiency of $R_2$ increases to 102%, the ratio $(1.02A_{22}*0.9A_{11})/(1.02A_{12}*0.9A_{21})$ will still equal $(A_3*A_1)/(A_2*A_4)$. Similarly, if the efficiency of transmitter $T_1$ reduces to 50% over the same period of time, the ratio $(1.02A_{22}*0.5*0.9A_{11})/(0.5*1.02A_{12}*0.9A_{22})$ will still equal $(A_3*A_1)/(A_2*A_4)$. Thus, the reduction in response cancels out and calculations based on the amplitude of the received signals are not affected by drift in either the transmitter or receiver. Compensated frequency shifts and arrival times are obtained using similar calculations. The frequency shift is $(\Delta f_1+\Delta f_2)/2$ and the arrival time is $[(\Delta t_{12}-\Delta t_{11})+(\Delta t_{21}-\Delta t_{22})]/2$. Hence the present invention can be operated for extended periods, even years, without requiring calibration or adjustment.

At present, there are no available in-situ sensors to detect, monitor or characterize solid deposition non-invasively. Because components of the sensor can be strapped on the outside of existing tubing, the invention can easily be retro-fitted onto existing pipelines and can be installed without disrupting flow through the pipeline. The present invention provides non-invasive and non-intrusive detection, identification, characterization and monitoring of deposits in real-time, and compensates for drift in the amplitude of the received signal. In a preferred embodiment, the invention also provides qualitative deposition monitoring over a length of pipe.

Using the apparatus and method described above, various embodiments of the present invention can be constructed, including but not limited to the following:

a guided acoustic wave sensor capable of detecting deposition of solids and semi-solids on the inner walls of pipes that are transporting crude petroleum;

a guided acoustic wave sensor capable of monitoring the thickness of a deposited layer that includes solids and semi-solids on the inner wall of a pipe;

a guided acoustic wave sensor capable of characterizing a material that is deposited on the inner wall of a pipe;

a guided acoustic wave sensor capable of monitoring deposit layer buildup and triggering alarms for remedial action in case the deposit layer exceeds a predetermined thickness;

a guided acoustic wave sensor that compensates for equipment response drift by using dual transmitters and receivers;

a guided acoustic wave sensor capable of finer detection, characterization and monitoring, using an array of receivers containing more than two sets of receivers along the pipe length as shown in FIG. 4; or a guided acoustic wave sensor capable of generating and detecting preferential modes of guided acoustic waves at various frequencies in the walls of the pipe, to isolate, detect and characterize deposition on the inner walls of the pipe.

Experimental Proof

The sensitivity of guided acoustic waves to surface deposition was examined in the following study. Guided acoustic waves were generated on a 1" pipe by creating a tone burst (S1) of 5 cycles at 300 kHz on an ultrasonic transducer. The generated waves traveled through the tubing and were recorded by two receivers $R_1$ and $R_2$. This procedure was repeated for three conditions as follows;

Example 1. With air on both the inside and outside of the pipe.

Example 2. With the pipe was completely filled with water on the inside, and surrounded by air on the outside.

Example 3. With the pipe completely filled with water and surrounded by air, and having a coating on the outside of the tubing of commercial wax applied to its central section.

Results from these experiments are tabulated in Tables 1 and 2. The Examples indicate that deposits were clearly detected by the sensors. Further experimentation showed that response of the guided acoustic waves was a function of the extent of the deposited wax layer (i.e., its length/area of coverage). Pipe end conditions did not affect the measurements.

TABLE 1

Amplitude At Various Measurements

| Measurement | Example 1 Air/Air | Example 2 Water/Air | Example 3 Water/Air + Wax |
|---|---|---|---|
| $A_{11}$ | 0.04 | 0.038 | 0.036 |
| $A_{12}$ | 0.04 | 0.035 | 0.0072 |
| $A_{21}$ | 0.042 | 0.035 | 0.0058 |
| $A_{22}$ | 0.043 | 0.037 | 0.036 |

TABLE 2 dB Loss

| | $A_{12}/A_{11}$ | $A_{21}/A_{22}$ | Change in dB |
|---|---|---|---|
| In Air | 1 | 0.98 | 0.088 |
| In Water | 0.92 | 0.95 | 0.585 |
| In Water with Wax | 0.2 | 0.16 | 14.95 |

Interpretation of Results

As shown in the data, the amplitude of the signal received at a given receiver is more greatly affected by distance from the transmitter in Example 3 than in the other Examples. Similarly, the attenuation coefficient will quickly reflect the solids build up on the inside wall of the pipeline. According to one embodiment of the invention, amplitude measurements such as these, and/or calculated attenuation coefficients can be collected for known systems and used to calibrate a measuring tool. The calibrated tool can then be used to determine the presence and/or thickness of deposits on the inside pipe wall. In addition, propagation and attenuation of specific modes of guided waves depend on the material properties of the deposition layer. By signaling and measuring the received signal at various frequencies, it becomes possible to characterize the deposits.

If it is expected that the pipeline that is being monitored may receive external deposits as well as internal deposits, as a result of the growth of living organisms or shifts in the seabed, for example, it may be desired to enclose at least a portion of the pipeline in a housing. The housing, which is preferably acoustically separate from the pipe wall and transducers, prevents the buildup of acoustically significant deposits on the outside of the pipe. By monitoring the enclosed portion of the pipeline in the manner described above, it is possible to obtain a set of benchmark measurements, which can then be used to calibrate or offset measurements that arrive from other, non-enclosed portions of the pipeline.

Similarly, a preferred embodiment of the present invention includes a microprocessor (not shown) for receiving and processing the signals received at the receiver. For example, the microprocessor can be programmed to store a predetermined number of sequential signals, so that the value of one or more parameters can be monitored over time. Comparison of each new data point to a moving average and/or to a benchmark value can be used to identify sudden changes in the measure parameter. Additionally, or alternatively, a time-averaged signal can be used, which has the effect of reducing noise in the signal and can be useful in tracking parameters that do not change suddenly, such as the thickness of a deposited layer. Likewise, when multiple transmitter/receiver sets are deployed along a length of pipeline, the microprocessor can be used to track all of the sets, compare them to a benchmark or to each other, and provide information about the location of deposits inside the pipe It is preferred that the present invention be used in conjunction with welded or coil tubing, so as to minimize the acoustic effect of upsets such as threaded connections.

While preferred embodiments of the present invention have been shown and described, it will be understood that various modifications can be made thereto without departing from the scope of the invention. Specifically, the number and configuration of the transmitters and receivers can be modified. The data sampling and data processing can be modified to include more data points and to include various signal processing, filtering, averaging and other mathematical techniques not specifically mentioned herein, and the frequency, amplitude and pulse length can each be varied, so long as they are operable in the present invention.

What is claimed is:

1. A system for monitoring the presence of deposits or buildup on the inside wall of a fluid-containing pipe, comprising:

first and second of acoustic transmitters outside of the pipe and spaced apart along the length of the pipe and capable of transmitting an acoustic signal into the pipe wall;

first and second of acoustic receivers outside of the pipe and spaced apart along the length of the pipe and capable of receiving an acoustic signal from the pipe wall;

a power source for causing said transmitters to transmit a signal; and a microprocessor adapted to receive information from said receivers, wherein the microprocessor calculates the attenuation of the signal over the length of pipe using the equation $$\alpha = \frac{1}{2X} \ln\left(\frac{A_{11}A_{22}}{A_{12}A_{21}}\right),$$

where X is the distance between the receivers, $A_{11}$ and $A_{12}$ are, respectively, the amplitudes of a signal from said first transmitter received at said first and second receivers, and $A_{21}$ and $A_{22}$ are, respectively, the amplitudes of a signal from said second transmitter received at said first and second receivers.

2. The pipeline monitoring system according to claim 1 wherein the microprocessor monitors the thickness of a deposited layer on the inner wall of the pipe.

3. The pipeline monitoring system according to claim 1 wherein the microprocessor characterizes the material that is deposited on the inner wall of the pipe.

4. The pipeline monitoring system according to claim 1 wherein the microprocessor monitors deposit layer buildup and triggering alarms for remedial action in case the deposit layer exceeds a pre-determined thickness.

5. The pipeline monitoring system according to claim 1 wherein the microprocessor compensates for equipment response drift by using dual transmitters and receivers.

6. The pipeline monitoring system according to claim 1 further including additional receivers between said transmitters.

7. The pipeline monitoring system according to claim 1 wherein the microprocessor detects preferential modes of guided acoustic waves at multiple frequencies in the walls of the pipe, so as to isolate, detect and characterize deposits on the inner walls of the pipe.

8. The pipeline monitoring system according to claim 1 wherein said first and second receivers are positioned between said transmitters.

9. The pipeline monitoring system according to claim 1, further including a housing preventing the buildup of acoustically interfering solids on the outside wall of the pipe.

10. A method for monitoring the presence of deposits or buildup on the inside wall of a fluid-containing pipe, comprising:

(a) providing first and second acoustic transmitters outside of the pipe and spaced apart along the length of the pipe and capable of transmitting an acoustic signal into the pipe wall;

(b) providing first and second acoustic receivers outside of the pipe and spaced apart along the length of the pipe and capable of receiving an acoustic signal from the pipe wall;

(c) transmitting a first signal from the first transmitter;

(d) measuring the amplitude of the first signal received at the first and second receivers as $A_{11}$ and $A_{12}$, respectively;

(e) transmitting a second signal from the second transmitter;

(f) measuring the amplitude of said second signal received at the first and second receivers as $A_{21}$ and $A_{22}$, respectively; and (g) calculating the attenuation of the signal over the length of pipe using the equation $$\alpha = \frac{1}{2X} \ln\left(\frac{A_{11}A_{22}}{A_{12}A_{21}}\right),$$

where X is the distance between the receivers.

11. The method according to claim 10, further including comparing the attenuation calculated in step (g) to a benchmark value that corresponds to a pipe free of deposits and buildup.

12. The method according to claim 10, further including recording the attenuation value and repeating steps (c) through (g) at a predetermined time increment.

13. The method according to claim 12, further including calculating a moving average of the attenuation.

14. The method according to claim 13, further including comparing the moving average to a benchmark value that corresponds to a pipe free of deposits and buildup.

15. The method according to claim 10, further including providing additional pairs of transmitters and receivers at known positions along the pipe and using the signal received from the additional receivers in combination with the known positions of the receivers to determine the position of the deposits or buildup.

16. The method according to claim 10, further including performing steps (c) through (g) at multiple frequencies and comparing the resulting attenuation measurements to a database so as to characterize the deposits or buildup.

17. The method according to claim 10, further including the step of detecting deposition of material on the inner walls of pipes that are transporting crude petroleum.

18. The method according to claim 10, further including monitoring the thickness of a deposited layer on the inner wall of a pipe.

19. The method according to claim 10, further including characterizing a material that is deposited on the inner wall of a pipe.

20. The method according to claim 10, further including monitoring deposit layer buildup and triggering alarms for remedial action when the deposit layer exceeds a predetermined thickness.

21. The method according to claim 10, further including compensating for equipment response drift by using dual transmitters and receivers.

22. The method according to claim 10, further including using an array of receivers containing more than two sets of receivers.

23. The method according to claim 10, further including generating and detecting preferential modes of guided acoustic waves at various frequencies in the walls of the pipe, to isolate, detect and characterize deposition on the inner walls of the pipe.

* * * * *